US006963776B2

(12) United States Patent
Seim

(10) Patent No.: US 6,963,776 B2
(45) Date of Patent: Nov. 8, 2005

(54) CARDIAC RHYTHM MANAGEMENT SYSTEM SYNCHRONIZING ATRIAL SHOCK TO VENTRICULAR DEPOLARIZATION BASED ON LENGTH OF SENSING REFRACTORY

(75) Inventor: Gary T. Seim, Minneapolis, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 492 days.

(21) Appl. No.: 09/826,973

(22) Filed: Apr. 5, 2001

(65) Prior Publication Data

US 2002/0147471 A1 Oct. 10, 2002

(51) Int. Cl.⁷ .............................................. A61N 1/362
(52) U.S. Cl. ...................................................... 607/14
(58) Field of Search ..................... 607/4–8, 12, 14–18, 607/25

(56) References Cited

U.S. PATENT DOCUMENTS

| | | | |
|---|---|---|---|
| RE30,387 E | 8/1980 | Denniston, III et al. .... | 128/419 |
| 5,042,480 A | 8/1991 | Hedin et al. .......... | 128/419 PG |
| 5,207,219 A | 5/1993 | Adams et al. .......... | 128/419 D |
| 5,282,836 A | 2/1994 | Kreyenhagen et al. ......... | 607/4 |
| 5,383,910 A | 1/1995 | den Dulk .................... | 607/14 |
| 5,395,373 A | 3/1995 | Ayers ......................... | 607/8 |
| 5,411,524 A * | 5/1995 | Rahul .......................... | 607/4 |
| 5,480,413 A | 1/1996 | Greenhut et al. ............ | 607/14 |
| 5,486,198 A | 1/1996 | Ayers et al. ................. | 607/5 |
| 5,545,182 A | 8/1996 | Stotts et al. .................. | 607/5 |
| 5,545,186 A | 8/1996 | Olson et al. ................. | 607/14 |
| 5,554,174 A | 9/1996 | Causey, III .................. | 607/5 |
| 5,584,864 A | 12/1996 | White .......................... | 607/5 |
| 5,591,215 A | 1/1997 | Greenhut et al. ............ | 607/14 |
| 5,674,250 A | 10/1997 | de Coriolis et al. ......... | 607/7 |
| 5,713,929 A | 2/1998 | Hess et al. ................... | 607/14 |

(Continued)

FOREIGN PATENT DOCUMENTS

| | | | |
|---|---|---|---|
| WO | 93/02746 | 2/1993 | .......... A61N/1/368 |
| WO | WO-97/11745 | 4/1997 | .......... A61N/1/362 |
| WO | 98/48891 | 11/1998 | .......... A61N/1/362 |

OTHER PUBLICATIONS

*Harmony, Automatic Dual Chamber Pacemaker, Product Information and Programming Guide*, Viatron Medical, Harmony Dual Chamber mentioned in publication Clinica, 467, p. 16, (Sep. 11, 1991), "Rate Devices Impact Pacemaker Market", and Clinica, 417, p. 9, (Sep. 5, 1990), "French CNH Equipment Approvals".,22 p.

Duckers, H..J. ,et al. ,"Effective use of a novel rate–smoothing algorithm in atrial fibrillation by ventricular pacing", *European Heart Journal, 18*, (1997),pp. 1951–1955.

Fahy, G..J. ,et al. ,"Pacing Strategies to Prevent Atrial Fibrillation", *Atrial Fibrillation, 14 (4)*, (Nov. 1996),pp. 591–596.

(Continued)

*Primary Examiner*—George Manuel
(74) *Attorney, Agent, or Firm*—Schwegman, Lundberg, Woessner & Kluth, P.A.

(57) ABSTRACT

A cardiac rhythm management system synchronizes the delivery of an atrial defibrillation shock to a ventricular depolarization concluding a present RR interval since the occurrence of the last ventricular depolarization. The present RR interval is deemed "shockable" if, among other things, its ventricular refractory period (VRP), which may be extended by ventricular "noise" occurring during the VRP, is less than a predetermined value, which may be different depending on whether the VRP is initiated by a paced or sensed ventricular depolarization. Alternatively, the present RR interval is deemed shockable if a post-VRP time period before the ventricular depolarization concluding the present RR interval exceeds a predetermined value. In conjunction with one or both of these conditions, other requirements for deeming a present RR interval shockable include comparing the present RR interval duration to a predetermined value, or to a preceding RR or QT interval.

20 Claims, 4 Drawing Sheets

U.S. PATENT DOCUMENTS

| | | | |
|---|---|---|---|
| 5,713,932 A | 2/1998 | Gillberg et al. | 607/27 |
| 5,776,164 A | 7/1998 | Ripart | 607/5 |
| 5,792,193 A | 8/1998 | Stoop | 607/14 |
| 5,814,081 A | 9/1998 | Ayers et al. | 607/5 |
| 5,814,085 A | 9/1998 | Hill | 607/14 |
| 5,836,975 A | 11/1998 | DeGroot | 607/5 |
| 5,840,079 A | 11/1998 | Warman et al. | 607/4 |
| 5,846,263 A | 12/1998 | Peterson et al. | 607/14 |
| 5,853,426 A | 12/1998 | Shieh | 607/5 |
| 5,855,593 A | 1/1999 | Olson et al. | 607/9 |
| 5,865,838 A | 2/1999 | Obel et al. | 607/5 |
| 5,873,897 A | 2/1999 | Armstrong et al. | 607/14 |
| 5,893,882 A | 4/1999 | Peterson et al. | 607/14 |
| 5,931,857 A | 8/1999 | Prieve et al. | 607/14 |
| 5,951,592 A | 9/1999 | Murphy | 607/4 |
| 5,968,079 A | 10/1999 | Warman et al. | 607/5 |
| 5,978,707 A | 11/1999 | Krig et al. | 607/14 |
| 5,983,138 A | 11/1999 | Kramer | 607/9 |
| 5,987,354 A | 11/1999 | Cooper et al. | 607/5 |
| 5,987,356 A | 11/1999 | DeGroot | 607/5 |
| 5,991,657 A | 11/1999 | Kim | 607/5 |
| 5,999,850 A | 12/1999 | Dawson et al. | 607/4 |
| 6,047,210 A | 4/2000 | Kim et al. | 607/4 |
| 6,081,745 A | 6/2000 | Mehra | 607/4 |
| 6,081,746 A | 6/2000 | Pendekanti et al. | 607/5 |
| RE36,765 E | 7/2000 | Mehra | 607/4 |
| 6,085,116 A | 7/2000 | Pendekanti et al. | 607/5 |
| 6,091,988 A | 7/2000 | Warman et al. | 607/5 |
| 6,249,699 B1 | 6/2001 | Kim | 607/4 |
| 6,256,534 B1 | 7/2001 | Dahl | 607/5 |
| 6,272,380 B1 | 8/2001 | Warman et al. | 607/5 |
| 6,285,907 B1 | 9/2001 | Kramer et al. | 607/9 |
| 6,430,438 B1 | 8/2002 | Chen et al. | 607/5 |
| 6,512,951 B1 * | 1/2003 | Marcovecchio et al. | 607/5 |
| 6,687,541 B2 | 2/2004 | Marcovecchio et al. | 607/5 |

OTHER PUBLICATIONS

Mehra, R., et al., "Prevention of Atrial Fibrillation/Flutter by Pacing Techniques", *Interventional Electrophysiology, Second Edition*, Chapter 34, Futura Publishing Company, Inc., (1996), pp. 521–540.

*Metrix Model 3020 Implantable Atrial Defibrillator*, Physician's Manual, InControl, Inc., Redmond, WA, pp. 4-24-4-27, (1998).

Ayers, G.M., et al., "Ventricular Proarrhythmic Effects of Ventricular Cycle Length and Shock Strength in a Sheep Model of Transvenous Atrial Defibrillation", *Circulation, 89 (1)*, pp. 413–422, (Jan. 1994).

Greenhut, S., et al., "Effectiveness of a Ventricular Rate Stabilization Algorithm During Atrial Fibrillation in Dogs", *Pace Abstract*, Abstract No. 60, 1 p., (1996).

Wittkampf, F., et al., "Rate Stabilization by Right Ventricular Pacing in Patients with Atrial Fibrillation", *Pace, 9*, pp. 1147–1153, (1986).

* cited by examiner

CARDIAC RHYTHM MANAGEMENT SYSTEM SYNCHRONIZING ATRIAL SHOCK TO VENTRICULAR DEPOLARIZATION BASED ON LENGTH OF SENSING REFRACTORY

CROSS REFERENCE TO RELATED APPLICATIONS

This application is related to the following co-pending, commonly assigned U.S. patent applications: "Cardiac Rhythm Management System With Atrial Shock Timing Optimization," Ser. No. 09/316,741 and "Method for Delivering Atrial Defibrillation Therapy," Ser. No. 09/661,875. The disclosure of each of these patent applications is herein incorporated by reference in its entirety.

TECHNICAL FIELD

The present system relates generally to cardiac rhythm management systems and particularly, but not by way of limitation, to such a system that synchronizes delivery of an atrial shock to a ventricular depolarization based at least in part on the nature of a refractory period following a ventricular depolarization.

BACKGROUND

When functioning properly, the human heart maintains its own intrinsic rhythm, and is capable of pumping adequate blood throughout the body's circulatory system. However, some people have irregular cardiac rhythms, referred to as cardiac arrhythmias. Such arrhythmias result in diminished blood circulation. One mode of treating cardiac arrhythmias uses drug therapy. Drugs are often effective at restoring normal heart rhythms. However, drug therapy is not always effective for treating arrhythmias of certain patients. For such patients, an alternative mode of treatment is needed. One such alternative mode of treatment includes the use of a cardiac rhythm management system. Such systems are often implanted in the patient and deliver therapy to the heart.

Cardiac rhythm management systems include, among other things, pacemakers, also referred to as pacers. Pacers deliver timed sequences of low energy electrical stimuli, called pace pulses, to the heart, such as via an intravascular leadwire or catheter (referred to as a "lead") having one or more electrodes disposed in or about the heart. Heart contractions are initiated in response to such pace pulses (this is referred to as "capturing" the heart). By properly timing the delivery of pace pulses, the heart can be induced to contract in proper rhythm, greatly improving its efficiency as a pump. Pacers are often used to treat patients with bradyarrhythmias, that is, hearts that beat too slowly, or irregularly. Such pacers coordinate atrial and ventricular contractions to improve pumping efficiency. Cardiac rhythm management systems also include coordination devices for coordinating the contractions of both the right and left sides of the heart for improved pumping efficiency.

Cardiac rhythm management systems also include defibrillators that are capable of delivering higher energy electrical stimuli to the heart. Such defibrillators also include cardioverters, which synchronize the delivery of such stimuli to portions of sensed intrinsic heart activity signals. Defibrillators are often used to treat patients with tachyarrhythmias, that is, hearts that beat too quickly. Such too-fast heart rhythms also cause diminished blood circulation because the heart isn't allowed sufficient time to fill with blood before contracting to expel the blood. Such pumping by the heart is inefficient. A defibrillator is capable of delivering a high energy electrical stimulus that is sometimes referred to as a defibrillation countershock, also referred to simply as a "shock." The countershock interrupts the tachyarrhythmia, allowing the heart to reestablish a normal rhythm for the efficient pumping of blood. In addition to pacers, cardiac rhythm management systems also include, among other things, pacer/defibrillators that combine the functions of pacers and defibrillators, drug delivery devices, and any other implantable or external systems or devices for diagnosing or treating cardiac arrhythmias.

One problem faced by cardiac rhythm management systems is the detection and treatment of atrial tachyarrhythmias, such as atrial fibrillation, in which one or both of the atrial heart chambers incoherently depolarizes in a rapid and chaotic fashion. Atrial fibrillation is a common cardiac arrhythmia that reduces the pumping efficiency of the heart, though not to as great a degree as ventricular fibrillation. However, this reduced atrial pumping efficiency forces the corresponding ventricle to work harder, which is particularly undesirable in sick patients that cannot tolerate additional stresses. Atrial fibrillation also causes variability in the ventricular heart rate, which is noticeable and uncomfortable for the patient. As a result of atrial fibrillation, patients must typically limit their activity and exercise.

Although atrial fibrillation, by itself, is usually not life-threatening, prolonged atrial fibrillation may be associated with strokes, which are thought to be caused by blood clots forming in areas of stagnant blood flow. Treating such blood clots may require the use of anticoagulants. Atrial fibrillation may also cause pain, tiredness, dizziness, and other irritation to the patient.

An even more serious problem, however, is the risk that atrial fibrillation may induce irregular ventricular heart rhythms by processes that are yet to be fully understood. Moreover, treatment of atrial fibrillation may also induce irregular ventricular heart rhythms. Such induced ventricular arrhythmias compromise pumping efficiency even more drastically than atrial arrhythmias and, in some instances, may be life-threatening. For these and other reasons, there is a need for safe and more effective treatment of atrial fibrillation that avoids inducing ventricular arrhythmias.

SUMMARY OF THE INVENTION

This document describes a cardiac rhythm management system that, among other things, synchronizes the delivery of an atrial defibrillation shock to a ventricular depolarization concluding a present RR interval since the occurrence of the last ventricular depolarization. The present RR interval is deemed "shockable" if, among other things, its ventricular refractory period (VRP), which may be extended by ventricular "noise" occurring during the VRP, is less than a predetermined value or, alternatively, if a post-VRP time period before the ventricular depolarization concluding the present RR interval exceeds a predetermined value. In conjunction with one or both of these conditions, other requirements for deeming a present RR interval shockable include comparing the present RR interval duration to a predetermined value, or to a preceding RR or QT interval. Also in conjunction with one or both of these conditions, is excluding from being shockable a present RR interval that is initiated by a paced ventricular depolarization and concluded by a sensed ventricular depolarization.

In one embodiment, the system includes a method in which an episode of atrial fibrillation is detected in an atrium. The system senses ventricular depolarizations, and measures a duration of a present RR interval since a most recent ventricular depolarization. The system delivers an atrial defibrillation shock synchronized to (albeit permissibly delayed a bit from) a ventricular depolarization, which concludes a present RR interval, if the present RR interval is shockable. A shockable present RR interval requires, among other things, that a ventricular sensing refractory period of the present RR interval is less than or equal to a first predetermined value or that a minimum sensing time period exists between the expiration of a ventricular refractory period (VRP) and a subsequent ventricular depolarization. The system also includes structures for performing this and other methods, as discussed below.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

Figure 1:
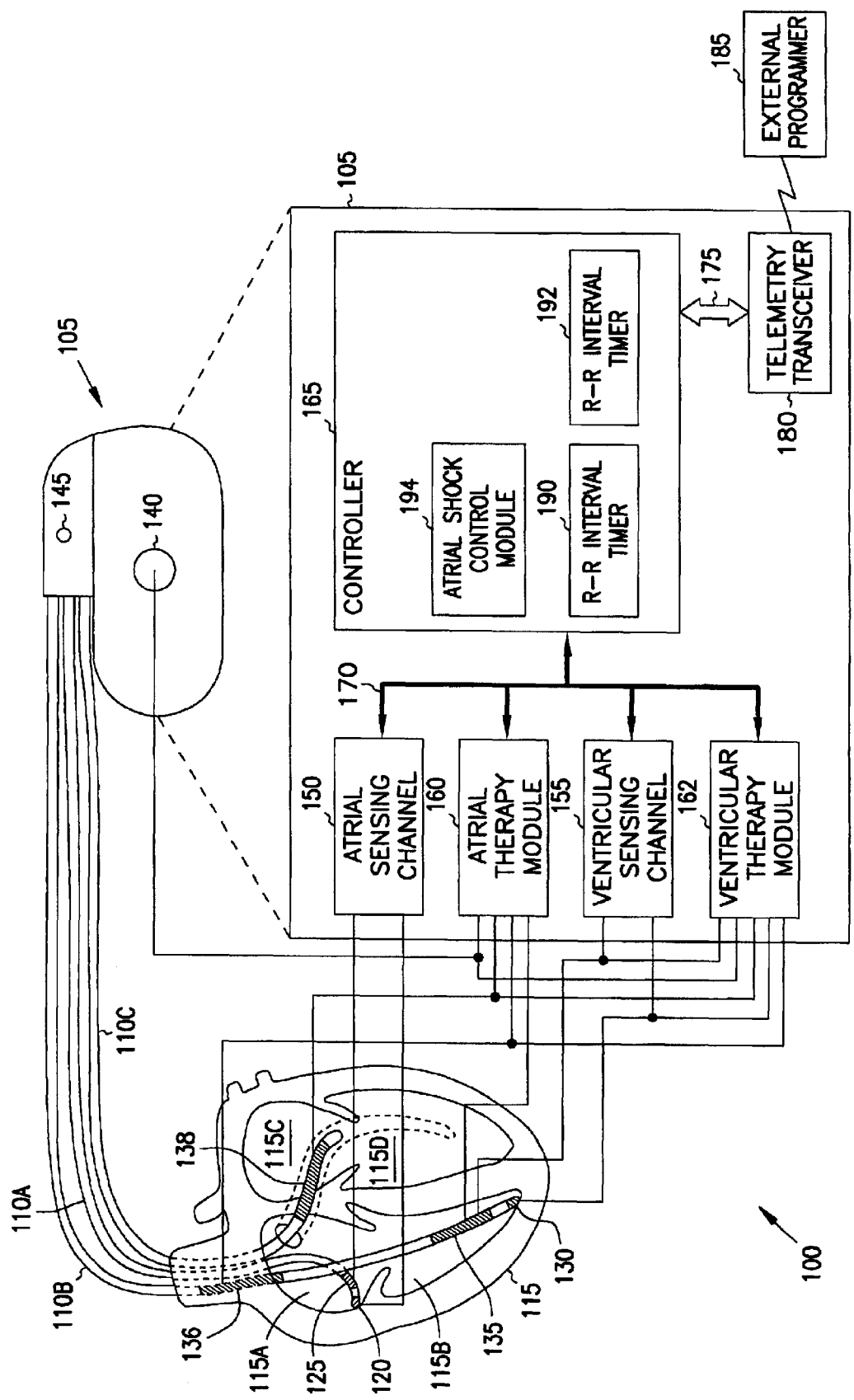
FIG. 1 is a schematic/block diagram illustrating generally, among other things, one embodiment of portions of a cardiac rhythm management system and an environment in which it is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents. In the drawings, like numerals describe substantially similar components throughout the several views. Like numerals having different letter suffixes represent different instances of substantially similar components. The term "and/or" refers to a nonexclusive "or" (i.e., "A and/or B" includes both "A and B" as well as "A or B").

This document discusses, among other things, a cardiac rhythm management system that synchronizes the delivery of an atrial defibrillation shock to a ventricular depolarization. As one example prerequisite to delivering the atrial shock, a ventricular sensing refractory period must not be extended beyond a first value. As an alternative example prerequisite, a time after expiration of the refractory period and before occurrence of a subsequent ventricular depolarization must exceed a second value. Other examples are also discussed. The present methods and apparatus will be described in applications involving implantable medical devices including, but not limited to, implantable cardiac rhythm management systems such as pacemakers, cardioverter/defibrillators, pacer/defibrillators, biventricular or other multi-site coordination devices, and drug delivery systems. However, it is understood that the present methods and apparatus may be employed in unimplanted devices, including, but not limited to, external pacemakers, cardioverter/defibrillators, pacer/defibrillators, biventricular or other multi-site coordination devices, monitors, programmers and recorders, whether such devices are used for providing a diagnostic, a therapy, or both a diagnostic and a therapy.

FIG. 1 is a schematic/block diagram illustrating generally one embodiment of portions of the present cardiac rhythm management system 100 and an environment in which it is used. In this embodiment, system 100 includes, among other things, a cardiac rhythm management device 105, which is coupled by one or more leads, such as 110A–C to heart 115. Heart 115 includes at least four chambers: right atrium 115A, right ventricle 115B, left atrium 115C, and left ventricle 115D.

In one embodiment, lead 110A includes an electrode associated with right atrium 115A, such as tip electrode 120 and/or ring electrode 125 for sensing atrial heart signals (including indications of atrial fibrillation) and/or providing atrial pacing pulses. The electrode is "associated" with the particular heart chamber by inserting it into that heart chamber, or by inserting it into a portion of the heart's vasculature that is close to that heart chamber, or by epicardially placing the electrode outside that heart chamber, or by any other technique of configuring and situating an electrode for sensing signals and/or providing therapy with respect to that heart chamber. Lead 110B includes an electrode, such as 130 or 135, for sensing ventricular heart signals and/or providing ventricular pacing pulses. In this example, lead 110B also includes an electrode, such as right ventricular electrode 135 and/or electrode 136 associated with a right atrium or superior vena cava (SVC), for providing a shock. Lead 110C includes an shock electrode 138 associated with a coronary sinus vessel extending from right atrium 115A toward left atrium 115C. Device 105 may also include other electrodes, such as housing electrode 140 and/or header electrode 145, which are useful for, among other things, unipolar sensing of heart signals and/or unipolar delivery of contraction-evoking pacing stimulations or defibrillation shocks in conjunction with one or more of the electrodes 120, 125, 130, 135, 136, and 138 associated with heart 115. Alternatively, bipolar sensing and/or pacing and/or defibrillation may be used, such as bipolar atrial sensing and/or pacing between electrodes 120 and 125, ventricular sensing and/or pacing between electrodes 130 and 135.

Device 105 includes a sensing module. The sensing module includes an atrial sensing channel 150 and a ventricular sensing channel 155, each of which is coupled to one or more of the electrodes for sensing electrical depolarizations, corresponding to heart chamber contractions. Such electrical depolarizations of the heart tissue include atrial depolarizations, referred to as P-waves, and ventricular depolarizations, referred to as QRS complexes. A typical QRS complex is a rapid sequence of three signal excursions away from a baseline in sequentially switching polarity, with the first excursion referred to as a Q-wave, the second (typically the largest) excursion referred to as an R-wave, and the third excursion referred to as the S-wave.

A ventricular heart signal also includes ventricular repolarizations, referred to as T-waves, which occur after respective QRS complexes in preparation for a subsequent ventricular contraction. In one embodiment, atrial sensing channel 150 includes a peak detector for detecting a P-wave peak, and ventricular sensing channel 155 includes a peak detector for detecting an R-wave peak. The atrial depolarizations sensed by atrial sensing channel 150 provide an indication of detected atrial arrhythmias, such as atrial fibrillation. Device 105 also includes an atrial therapy module 160, coupled to one or more electrodes for delivering an atrial defibrillation shock to interrupt an episode of atrial fibrillation detected by atrial sensing channel 150. In one example, the atrial defibrillation shock is delivered between: (1) the housing electrode 140; and (2) the commonly connected left ventricular shock electrode 135 and superior vena cava electrode 136. In another example, the atrial defibrillation shock is delivered between: (1) the housing electrode 140; and (2) the commonly connected superior vena cava electrode 136 and coronary sinus electrode 138. In one embodiment, device 105 also includes a ventricular therapy module 162, coupled to one or more ventricular electrodes, such as electrodes 130 and/or 135, for delivering a ventricular pacing pulse to induce a ventricular heart contraction. In a further embodiment, ventricular therapy module 162 is coupled to one or more electrodes, such as electrodes 135, 136, and 140 for delivering ventricular defibrillation shocks to interrupt an episode of ventricular fibrillation detected by ventricular sensing channel 155.

Device 105 also includes a controller 165 or other microsequencer capable of executing instructions. Controller 165 is coupled by bus 170 to atrial sensing channel 150, ventricular sensing channel 155, atrial therapy module 160 and ventricular therapy module 162. In one embodiment, controller 165 is also coupled by bus 175 to telemetry transceiver 180, which is configured for wireless communication with a remote device, such as external programmer 185.

Controller 165 includes an RR interval timer 190. RR interval timer 190 measures a present RR interval since the last ventricular contraction. The present RR interval is initiated either by the last R-wave detected by ventricular sensing channel 155 (or by the delivery of a ventricular pacing pulse by ventricular therapy module 162). The present RR interval measures the time since the last sensed or paced ventricular contraction up to the present point in time. RR interval timer 190 is reset by the next sensed or paced ventricular contraction, which concludes the present RR interval, and which initiates a new present RR interval. In one embodiment, controller 165 also includes one or more memory locations for storing one or more respective previous values of the RR interval for earlier cardiac cycles.

Controller 165 also includes a ventricular refractory timer 192. The ventricular refractory timer times a ventricular sensing refractory period ("ventricular refractory period" or "VRP") that is initiated by the last R-wave detected by ventricular sensing channel 155 (or by the delivery of a ventricular pacing pulse by ventricular therapy module 162). The ventricular refractory period expires after a default time duration (which may be different depending upon whether the ventricular refractory period was initiated by a sensed ventricular depolarization or a paced ventricular depolarization), unless the ventricular refractory period is extended beyond its default duration, such as discussed below. During the ventricular refractory period, ventricular heart signals detected as ventricular depolarizations by ventricular sensing channel 155 are deemed "noise," rather than being recognized as a valid ventricular depolarization that would, among other things, reset the RR interval timer. For example, without the VRP, an early portion of a QRS complex could be recognized as a ventricular depolarization, thereby resetting the RR interval timer, and a later portion of the same portion of the QRS complex could potentially be erroneously detected as a subsequent ventricular depolarization event. Ignoring sensed ventricular heart activity during the VRP avoids falsely detecting such heart activity as ventricular depolarizations and resetting the RR interval timer. In one embodiment, detection of such "noise" during the ventricular refractory period may extend the duration of the ventricular refractory period beyond its default duration, such as discussed below.

Controller 165 also includes an atrial shock control module 194 that, among other things, controls the delivery of an atrial shock by atrial therapy module 160 in response to the detection of an episode of atrial fibrillation by atrial sensing channel 150. The atrial shock is delivered synchronous to a ventricular depolarization concluding the present RR interval if, among other things, the present RR interval is deemed "shockable," the criteria for which is discussed below.

Figure 2:
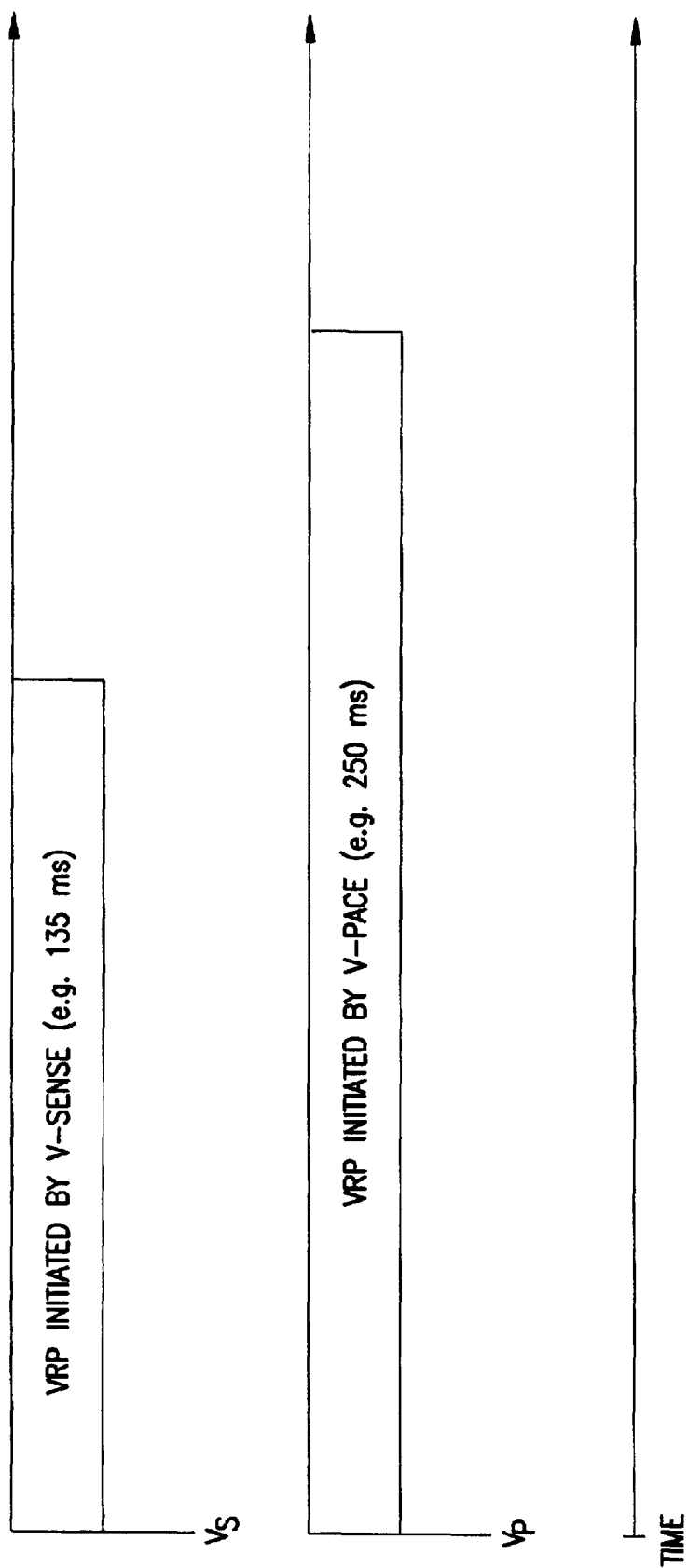
FIG. 2 is a timing diagram illustrating generally operation of example ventricular refractory periods ("VRPs").

FIG. 2 is a timing diagram illustrating generally operation of one embodiment of ventricular refractory timer 192 that provides a VRP. During the VRP, sensed ventricular heart activity is deemed noise. Such activity during a VRP is not deemed to be valid ventricular depolarization events, but is instead ignored. Sensed ventricular heart activity detected by ventricular sensing channel 155 after expiration of the VRP is deemed a valid ventricular depolarization if the sensed waveform meets a ventricular sensing criterion (e.g., amplitude, frequency, and/or other characteristics associated with a ventricular depolarization). FIG. 2 illustrates a (e.g., 135 millisecond) default VRP initiated by a valid sensed ventricular depolarization, denoted $V_s$, and a longer (e.g., 250 millisecond) default VRP initiated by a ventricular pace. In this embodiment, the default value of a pace-initiated VRP is longer than the default value of a sense-initiated VRP; alternatively, the default value of a pace-initiated VRP could be set equal to that of a sense-initiated VRP.

Figure 3:
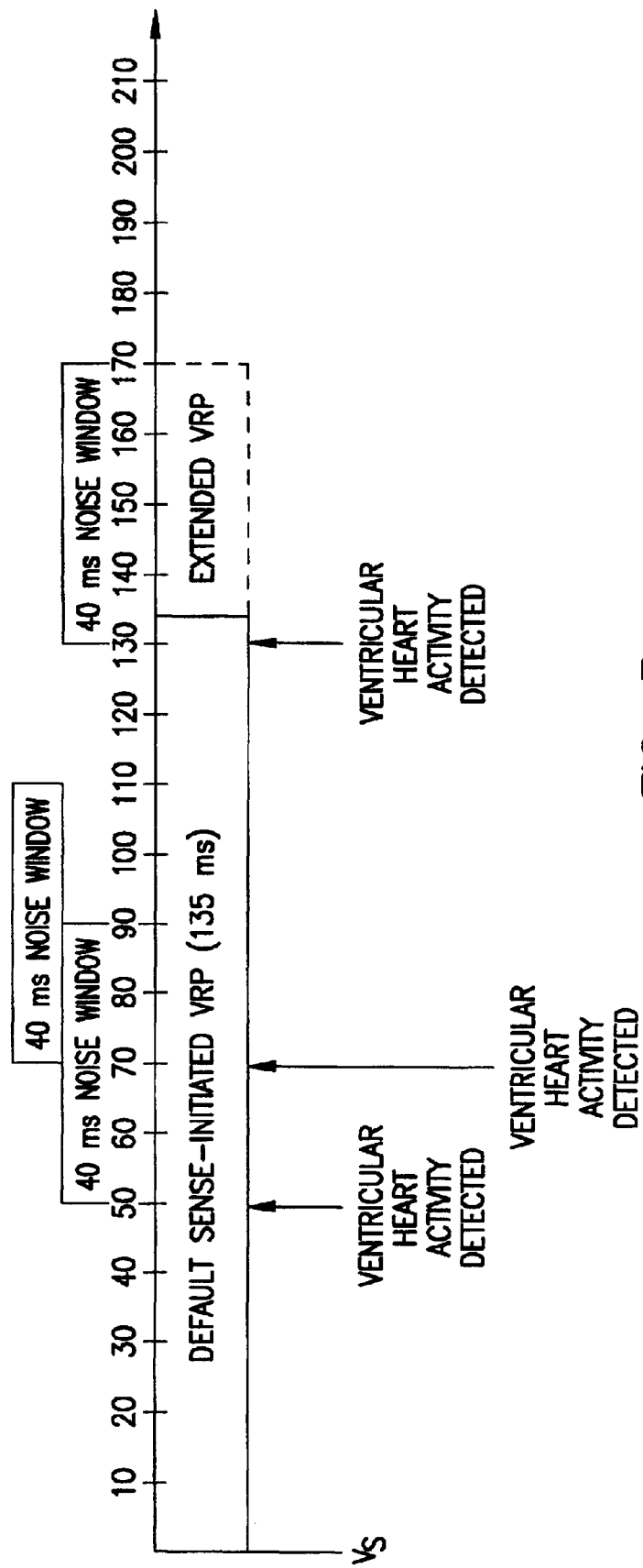
FIG. 3 is a timing diagram illustrating generally examples of noise windows and of extending a ventricular refractory period.

The VRPs illustrated in FIG. 2 are subject to being extended beyond their default values. FIG. 3 is a timing diagram providing an example of how ventricular heart activity detected by ventricular sensing channel 155 during a VRP is deemed noise that triggers an (e.g., 40 millisecond) noise window following the detection of the event that is deemed noise. As with the VRP, ventricular heart activity is ignored during the noise window. Moreover, the noise window is used in combination with the VRP and, if the noise window occurs late enough in the VRP, extends the VRP until the time at which the noise window expires. In the example of FIG. 3, ventricular heart activity is detected 50 milliseconds after the ventricular sense, which triggers a 40 millisecond noise window that expires at 90 milliseconds after the ventricular sense. FIG. 3 also illustrates that ventricular heart activity occurring during this noise window, at 70 milliseconds after the ventricular sense, triggers another noise window that expires at 110 milliseconds after the ventricular sense. FIG. 3 also illustrates that ventricular heart activity occurring at 130 milliseconds triggers a noise window that extends the ventricular refractory period beyond its default value of 135 milliseconds until the noise window expires at 170 milliseconds after the ventricular sense. Other detection of ventricular heart activity during the noise-window extended VRP would similarly trigger a (e.g., 40 millisecond) noise window further extending the VRP.

As discussed above, device 105 delivers an atrial shock synchronous to the next (paced or sensed) ventricular contraction to interrupt an episode of atrial fibrillation, provided that the present RR interval (i.e., the time since the last sensed or paced ventricular contraction) is deemed "shockable." In one embodiment, a shockable RR interval requires, among other things, that a VRP associated with the present RR interval must be less than or equal to a first predetermined value. In this example, a sensed ventricular contraction triggers a different default VRP than a paced ventricular contraction. A sensed ventricular contraction typically triggers a default VRP that is set at approximately between 95 milliseconds and 250 milliseconds, such as about 135 milliseconds. A paced ventricular contraction typically triggers a default VRP that is set at approximately between 150 milliseconds and 500 milliseconds, such as about 250 milliseconds. As discussed above, noise sensed during the VRP may extend the VRP from its default value. In one embodiment, the first predetermined value to which the VRP is compared for a sense-triggered VRP is different from the first predetermined value to which the VRP is compared for a pace-triggered VRP, such as where the default VRP values are different depending on whether sense-triggered or pace-triggered, as in the example of FIG. 2. In one embodiment, the first predetermined value is set equal to the default sense-triggered VRP when the present RR interval is initiated by a sensed ventricular depolarization, and set equal to the default pace-triggered VRP when the present RR interval is initiated by a paced ventricular depolarization. In such an example, any noise-window extension of the VRP will result in the present RR interval being deemed "not shockable."

For a sensed-triggered VRP, the first predetermined value is set at the same value as the default sense-triggered VRP (e.g., at about 135 milliseconds in the example of FIG. 3); if the VRP exceeds this value (such as by noise-window extension), the present RR interval is deemed "not shockable," and delivery of the atrial shock is delayed until a subsequent cardiac cycle. For example, in the scenario illustrated in FIG. 3, in which the VRP is extended beyond 135 milliseconds to 170 milliseconds due to the illustrated noise window, the present RR interval initiated by the illustrated ventricular sense would be deemed not shockable because of its extension beyond the 135 millisecond default sensed VRP.

For a pace-triggered VRP, the first predetermined value is set at the same value as the default pace-triggered VRP (e.g., at about 250 milliseconds in the example of FIG. 2); if the VRP exceeds this value (such as by noise-window extension), the present RR interval is deemed "not shockable," and delivery of the atrial shock is delayed until a subsequent cardiac cycle.

In one embodiment, the shockable present RR interval requirement of a ventricular refractory period is less than or equal to a first predetermined value is used in conjunction with at least one other condition for deeming the present RR interval to be shockable. Marchovecchio et al. U.S. patent application Ser. No. 09/661,875 entitled "Method for Delivering Atrial Defibrillation Therapy," and assigned to Cardiac Pacemakers, Inc., which is incorporated herein by reference in its entirety, sets forth additional conditions for deeming a present RR interval to be shockable. One such condition, used in conjunction with the instant requirement that the ventricular refractory period is less than or equal to a first predetermined value, is that the present RR interval duration must be longer than a preceding QT interval (i.e., between the Q-wave of the ventricular depolarization and a subsequent T-wave associated with a ventricular repolarization) duration by a second predetermined value (e.g., a second predetermined value providing a therapy margin that is approximately between 0 milliseconds and 200 milliseconds, such as about 60 milliseconds). The preceding QT interval need not be measured, it can instead be estimated from the measured value of the preceding RR interval (i.e., the RR interval concluded by the most recently detected (or paced) ventricular contraction and initiated by an immediately preceding paced or sensed ventricular contraction. A second, alternative, condition used in conjunction with the instant requirement that the ventricular refractory period is less than or equal to a first predetermined value, is that the present RR interval duration is longer than the preceding QT interval by the second predetermined value (or some other therapy margin), and the present RR interval duration is longer than a third predetermined value (e.g., a third predetermined value providing a minimum interval duration that is approximately between 350 milliseconds and 1000 milliseconds, such as about 500 milliseconds). A third, alternative, condition used in conjunction with the instant requirement that the ventricular refractory period is less than or equal to a first predetermined value, is that the present RR interval duration is longer than a fourth predetermined value, in which the fourth predetermined value is greater than the third predetermined value. In one embodiment, the fourth predetermined value is a minimum interval duration that is approximately between 500 milliseconds and 1000 milliseconds, such as about 700 milliseconds, or such as about 800 milliseconds.

Chen et al. U.S. patent application Ser. No. 09/316,741 entitled "Cardiac Rhythm Management System With Atrial Shock Timing Optimization," and assigned to Cardiac Pacemakers, Inc., which is incorporated herein by reference in its entirety, sets forth additional conditions for deeming a present RR interval to be shockable. One such condition, used in conjunction with the instant requirement that the ventricular refractory period is less than or equal to a first predetermined value, is that the present RR interval duration is longer than the preceding RR interval by a fifth predetermined value (e.g., a fifth predetermined value that is approximately between 0 milliseconds and 200 milliseconds, such as about 90 milliseconds), and the present RR interval duration is longer than a sixth predetermined value (e.g., the sixth predetermined value providing a minimum interval that is approximately between 350 milliseconds and 1000 milliseconds, such as about 500 milliseconds). A second such condition, used in conjunction with the instant requirement that the ventricular refractory period is less than or equal to a first predetermined value, is that the present RR interval duration is longer than a seventh predetermined value (e.g., a seventh predetermined value that is approximately between 500 milliseconds and 1000 milliseconds, such as about 700 milliseconds or 800 milliseconds, in which the seventh predetermined value is greater than the sixth predetermined value.

Another possible condition, used in conjunction with the instant requirement that the ventricular refractory period is less than or equal to a first predetermined value, is that the present RR interval's initiating and concluding ventricular depolarizations not be paced and sensed, respectively. In such a situation, where the present RR interval is initiated by a paced ventricular depolarization, and the present RR interval is concluded by a sensed ventricular depolarization, the present RR interval is deemed "not shockable," and delivery of the atrial shock is delayed until a subsequent cardiac cycle.

Figure 4:
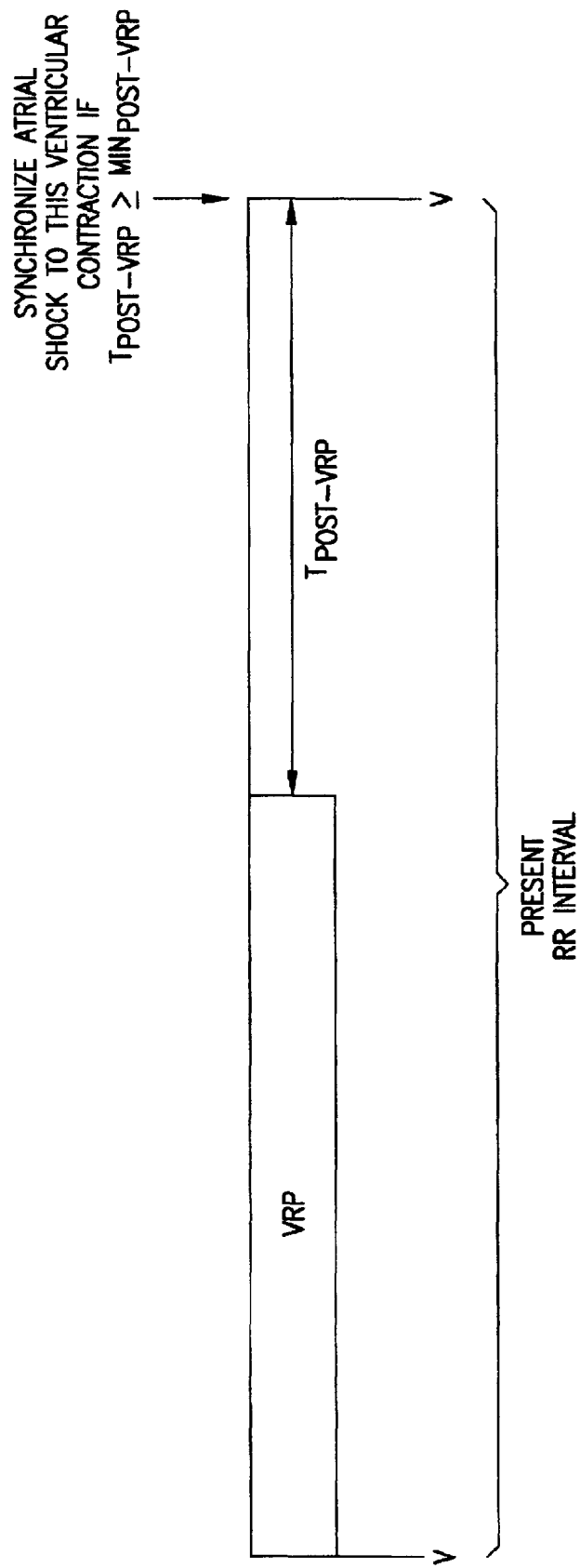
FIG. 4 is a timing diagram illustrating generally examples of a post ventricular refractory period criterion for determining whether a present RR interval since the last ventricular depolarization should be deemed "shockable."

In an alternative embodiment, the instant requirement that the ventricular refractory period is less than or equal to a first predetermined value, is replaced by an alternative requirement that a post-refractory ventricular sensing period (i.e., between expiration of the ventricular refractory period and the subsequent sensed or paced ventricular contraction) exceeds an eighth predetermined value (e.g., an eighth predetermined value that is approximately between 265 milliseconds and 565 milliseconds such as about 365 milliseconds). This ensures a sufficiently long post-VRP ventricular sensing period for detecting a ventricular heart contraction (or alternatively, delivering a ventricular pacing pulse if the present RR interval exceeds an "escape interval" timeout corresponding to the indicated heart rate being maintained by the device 105). This is illustrated in FIG. 4 by requiring that the post-VRP ventricular sensing time period, $T_{POST-VRP}$, equals or exceeds a minimum required value, $MIN_{POST-VRP}$ that is approximately between 265 milliseconds and 565 milliseconds, such as about 365 milliseconds. In one embodiment, if minimum ventricular sensing time period requirement is met, then the present RR interval is deemed shockable and an atrial shock is delivered synchronous to (although permissibly delayed a bit from) the ventricular event concluding the present RR interval, as illustrated in FIG. 4. Other requirements may be imposed in conjunction with this requirement for delivering the atrial shock, such as discussed above with respect to the maximum VRP requirement.

Conclusion

This document describes a cardiac rhythm management system that, among other things, synchronizes the delivery of an atrial defibrillation shock to a ventricular depolarization if the present RR interval is deemed shockable. Possible prerequisites for deeming the present RR interval shockable include, among other things, determining whether a ventricular refractory period exceeds a particular value, or determining whether a post-ventricular sensing period exceeds a particular value.

It is to be understood that the above description is intended to be illustrative, and not restrictive. For example, the above-described embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein."

What is claimed is:

1. A method including:
   detecting an episode of atrial fibrillation in an atrium;
   sensing ventricular depolarizations;
   measuring a duration of a present RR interval since a most recent ventricular depolarization;
   delivering an atrial defibrillation shock synchronized to a ventricular depolarization, which concludes a present RR interval, if the present RR interval is shockable, where a shockable present RR interval requires that a ventricular sensing refractory period of the present RR interval is less than or equal to a first predetermined value.

2. The method of claim 1, in which the first predetermined value provides different values if the present RR interval is initiated by a sensed ventricular depolarization than if the present RR interval is initiated by a paced ventricular depolarization.

3. The method of claim 1, in which the shockable present RR interval also requires that the present RR interval is not both initiated by a paced ventricular depolarization and concluded by a sensed ventricular depolarization.

4. The method of claim 1, in which the shockable present RR interval also requires at least one of:
   (A) the present RR interval duration is longer than a preceding QT interval duration by a second predetermined value;
   (B) the present RR interval duration is longer than the preceding QT interval by the second predetermined value, and the present RR interval duration is longer than a third predetermined value;
   (C) the present RR interval duration is longer than a fourth predetermined value, in which the fourth predetermined value is greater than the third predetermined value;
   (D) the present RR interval duration is longer than a preceding RR interval by a fifth predetermined value, and the present RR interval duration is longer than a sixth predetermined value; and
   (E) the present RR interval duration is longer than a seventh predetermined value, in which the seventh predetermined value is greater than the sixth predetermined value.

5. The method of claim 4, in which the preceding QT interval, $QT_{n-1}$, is estimated as a function of a preceding RR interval, $RR_{n-1}$.

6. The method of claim 5, in which $QT_{n-1}$ is estimated as:

$$QT_{n-1} = K \cdot \ln(RR_{n-1}) - C$$

where K and C are defined constants and $RR_{n-1}$ is the measured preceding RR interval.

7. The method of claim 6, in which K and C are defined as approximately 166.2 and 715.5, respectively.

8. The method of claim 6, in which K and C are defined as approximately 185.5 and 812.3, respectively.

9. The method of claim 4, in which the second predetermined value is approximately equal to 60 milliseconds.

10. The method of claim 1, in which the first predetermined value is approximately equal to 135 milliseconds.

11. A system comprising:
    an atrial sensing channel, configured for detecting an atrial heart signal indicating a presence of atrial fibrillation;
    a ventricular sensing channel, configured for detecting a ventricular heart signal including ventricular depolarizations indicating ventricular contractions;
    a shock generator, for generating an atrial defibrillation shock;
    a controller, coupled to the atrial sensing channel for receiving the atrial heart signal, coupled to the ventricular sensing channel for receiving the ventricular heart signal, and coupled to the shock generator for triggering delivery of the atrial defibrillation shock, the controller including:
       a ventricular sensing refractory timer, initiating a present refractory period, $T_n$, upon occurrence of a most recent ventricular depolarization, the refractory period expiring after a first predetermined time value unless extended by the detection of ventricular noise during the refractory period; and
       a present RR interval, $RR_n$, timer initiated by the most recent ventricular depolarization and expiring upon a subsequent sensed or paced ventricular depolarization; and
    wherein the triggering delivery of the atrial defibrillation shock occurs upon expiration of the present RR interval timer and requires that the refractory period $T_n$ expires without being extended.

12. The system of claim 11, in which the triggering delivery of the atrial defibrillation shock also requires that the present RR interval is not both initiated by a paced ventricular depolarization and concluded by a sensed ventricular depolarization.

13. The system of claim 11, in which the first predetermined time value provides different values if the present RR interval is initiated by a sensed ventricular depolarization than if the present RR interval is initiated by a paced ventricular depolarization.

14. The system of claim 11, in which the triggering delivery of the atrial defibrillation shock also requires at least one of:

(A) the present RR interval is longer than a preceding QT interval by a second predetermined value;

(B) the present RR interval duration is longer than the preceding QT interval by the second predetermined value, and the present RR interval duration is longer than a third predetermined value;

(C) the present RR interval duration is longer than a fourth predetermined value, in which the fourth predetermined value is greater than the third predetermined value;

(D) the present RR interval duration is longer than a preceding RR interval by a fifth predetermined value, and the present RR interval duration is longer than a sixth predetermined value; and (E) the present RR interval duration is longer than a seventh predetermined value, in which the seventh predetermined value is greater than the sixth predetermined value.

15. The system of claim 14, in which the controller estimates the preceding QT interval, $QT_{n-1}$, as a function of a preceding RR interval, $RR_{n-1}$.

16. The system of claim 15, in which the controller estimates $QT_{n-1}$ as:

$$QT_{n-1} = K \cdot \ln(RR_{n-1}) - C$$

where K and C are defined constants and $RR_{n-1}$ is the measured preceding RR interval.

17. The system of claim 15, in which K and C are defined as approximately 166.2 and 715.5, respectively.

18. The system of claim 15, in which K and C are defined as approximately 185.5 and 812.3, respectively.

19. The system of claim 14, in which the second predetermined value is approximately equal to 60 milliseconds.

20. The system of claim 11, further including at least one of: (A) an atrial electrode; (B) a ventricular electrode; and (c) a programmer remote from the controller and communicatively coupled thereto.

* * * * *